United States Patent [19]

Wuts

[11] Patent Number: 5,011,976
[45] Date of Patent: Apr. 30, 1991

[54] INTERMEDIATE FOR THE PREPARATION OF DEFEROXAMINE

[75] Inventor: Peter G. M. Wuts, Galesburg, Mich.

[73] Assignee: The Upjohn Company, Kalamazoo, Mich.

[21] Appl. No.: 548,717

[22] Filed: Jul. 6, 1990

[51] Int. Cl.$^5$ ............................................. C07C 271/00
[52] U.S. Cl. ...................................... 560/159; 560/31; 560/32
[58] Field of Search ............................ 560/31, 32, 159

[56] References Cited

U.S. PATENT DOCUMENTS 3,576,844  4/1971  Ishida et al. ........................ 560/159

Primary Examiner—James H. Reamer
Attorney, Agent, or Firm—Donald L. Corneglio

[57] ABSTRACT

An intermediate useful in the preparation of deferoxamine having Formula I $$X-Ph-CH_2-O-C(O)-NH-(CH_2)_4CH=NOR$$

wherein X is a $C_1$-$C_4$ alkyl, $-O(C_1$-$C_4$ alkyl), a halogen or hydrogen; R is $X-Ph-CH_2-$ or hydrogen. In one embodiment X and R are hydrogen. The intermediate has the advantage of being prepared in fewer and more efficient steps from readily available materials than conventional means for preparing deferoxamine.

5 Claims, No Drawings

INTERMEDIATE FOR THE PREPARATION OF DEFEROXAMINE

BACKGROUND OF THE INVENTION

The present invention is directed toward a novel, key intermediate for the preparation of deferoxamine. Deferoxamine is well known in the art as a natural product which is microbial iron chelator and was first isolated from Streptomyces pilosus which utilized it to obtain iron from the environment. Its synthesis and characterization were documented by Bickel (*Helv. Chim. Acta.*, Vol.43. p. 2129) in 1960. Deferoxamine has various pharmaceutical uses such as the treatment of hemodialysis-induced aluminum accumulation in the brain and for iron overload conditions.

The synthesis of deferoxamine and its analogs has been described in various publications such as U.S. Pat. Nos. 3,471,476 and 3,247,197 and European patent application No. 0 347 163 published 20 Dec. 1989. Despite the various methods disclosed for the synthesis of deferoxamine new and more economical means for synthesis have been sought. The present invention discloses a key intermediate which can be prepared from readily available ingredients and using conventional chemistry. This provides a distinct advantage over previous methods for the synthesis of deferoxamine which have required the use sensitive chemical procedures or difficult to prepare intermediates.

INFORMATION DISCLOSURE STATEMENT

Various synthesis methods for preparing deferoxamine are described in publications such as Bickel, *Helv. Chim. Acta.*, 43 2129 (1960); *Helv. Chim. Acta.*, 45 631 (1962); and R. J. Bergerson and J. J. Pegram, *J. Org. Chem.*, 53 3131 (1988).

U.S. Pat. Nos. 3,118,823; 3,153,621; 3,158,552; 3,247,197 and 3,471,476 describe the general state of the art with respect to deferoxamine. The latter two deal with the chemical synthesis of deferoxamine. European patent application publication to the University of Florida publication number 0 347 163 also describes the chemistry of deferoxamine similar to that of Bergerson.

SUMMARY OF THE INVENTION

In one aspect, the subject invention is an intermediate useful in the preparation of deferoxamine having Formula I

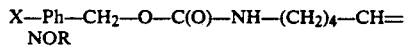

wherein X is a $C_1$-$C_4$ alkyl, $-O(C_1$-$C_4$ alkyl), a halogen or hydrogen; R is X—Ph—$CH_2$—or hydrogen. In one preferred embodiment X and R are independently hydrogen or X is a methyl or methoxy group. In another preferred embodiment X and R are hydrogen.

The intermediate has the advantage of being prepared in fewer and more efficient steps from readily available materials than conventional means for preparing deferoxamine.

DETAILED DESCRIPTION OF THE INVENTION

The present invention is directed toward a key intermediate for the preparation of deferoxamine (also referred to as desferrioxamine). Desferrioxamine B (12 in Schemes, below) is an excellent chelator for iron ($K_f = 10^{30}$ $M^{-1}$) and is used to treat diseases such as thalassemias. The intermediate is shown as Formula I:

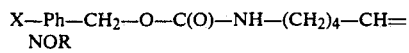

wherein "X" is a $C_1$-$C_4$ alkyl, $-O(C_1$-$C_4$ alkyl), a halogen (Cl, Br, F or I) or hydrogen any of which can be located at any of the positions on the phenyl ring (Ph); and where "R" is X—Ph—$CH_2$— or hydrogen. A "$C_1$-$C_4$ alkyl" is methyl, ethyl, propyl or butyl including isomeric forms thereof. Methyl is a preferred alkyl. A preferred intermediate is where X and R are individually or simultaneously hydrogen which would be 1-carbobenzoxyamino-5-hydroxyliminopentane.

The subject intermediate is shown in Scheme I and II as oxime 6. It can be used to prepare the siderophore desferrioxamine 12.

Desferrioxamine was prepared from the subject intermediate oxime 6 as outlined in the Scheme I. The oxime can also be prepared as outlined in scheme II. While the electrolysis reaction is not new the conversion of the amide to the oxime is. This sequence differs from that in Scheme I by replacement of the OH with an O-methyl group. Subsequent transformations of the oxime to the amides 8 and 9 proceed via generally recognized methodology. The conversion of the hydroxamic acid 8 to the cyclic mixed anhydride 10 has been done with DCC or acetic anhydride as coupling agents. The conversion also proceeds with diisopropylcarbodiimide (DIC) or with a hindered acid chloride in the presence of base to form the cyclic mixed anhydride which is then used in the coupling steps. The use of DIC is an extension of the use of DCC. Another excellent means for forming the cyclic mixed anhydride is with isobutylchloroformate.

PREPARATION OF INTERMEDIATE, OXIME (6)

A solution of piperidine 60 ml, acetic acid 51 ml and water 50 ml was prepared. This solution was then added to a slurry of Ca(OCl)$_2$, 150 ml MTBE (methyl t-butyl ether) and 75 ml of water keeping the temperature between 0° and 10° C. When the addition is complete the solution was stirred for an additional 20 minutes. The chloramine was then isolated with MTBE (2 × 150 mL). The combined MTBE layers were concentrated to 110 ml and this solution was slowly added to a slurry of 45 g of KOH in 100 ml of MeOH keeping the temperature between 20° and 27° C. Potassium chloride precipitates from the mixture. The mixture is kept at room temperature overnight and then treated with 150 ml of saturated NaHCO$_3$. The BnOC(O)Cl is slowly added. The pH starts at about 14 and slowly drops as the BnOC(O)Cl is added. When the pH reaches 9, 50% NaOH is added to keep it between 9 and 10. When the addition is complete stir the solution for 1 or more hours and then extract with 3 × 100 mL of MTBE. The combined MTBE layers were dried over magnesium sulfate, filtered and concentrated to a pale yellow oil. The crude amide is taken up in 200 ml of MeOH and 100 ml of pyridine and treated with 44 g of hydroxylamine hydrochloride at reflux for 4 hours. MeOH was distilled from the mixture. After cooling the solution to $\sim 35°$ C., 400 ml of water was slowly added to knock out the oxime. The crystals were washed with water and MTBE and then dried with nitrogen to afford 69 g. of oxime, 48% yield. In general the yield of this reaction varies between about 45-65%. It should be noted that the initial conversion to the chloramine is not limited by the reaction described and that there are a number of other methods that can be used to accomplish this transformation.

The subject intermediate is prepared in efficient steps described above from readily available materials and represents an economical means for preparing deferoxamine.

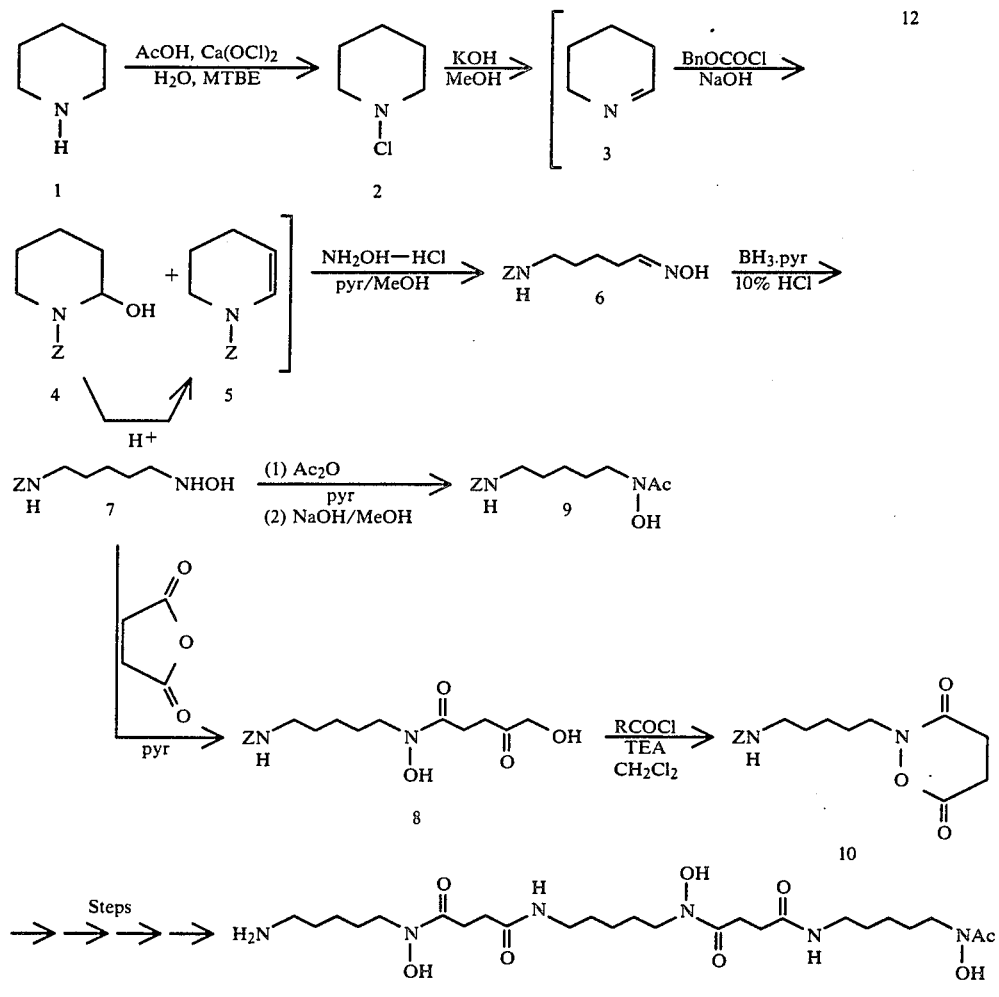

Scheme I

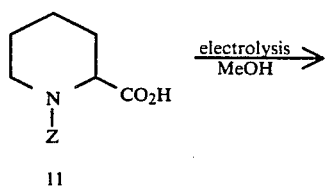

Scheme II

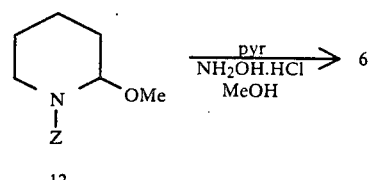

-continued
Scheme II

What is claimed:
1. A compound of Formula I

X—Ph—CH$_2$—O—C(O)—NH—(CH$_2$)$_4$—CH=NOR wherein
X is a C$_1$-C$_4$ alkyl, —O(C$_1$-C$_4$ alkyl), a halogen or hydrogen;
R is X—Ph—CH$_2$— or hydrogen.
2. The compound of claim 1 wherein R is hydrogen.
3. The compound of claim 1 wherein X is hydrogen.
4. The compound of claim 1 wherein X is a methyl or methoxy.
5. The compound of claim 1 wherein X and R are hydrogen.

* * * * *